(12) United States Patent
Lizzi

(10) Patent No.: US 6,264,930 B1
(45) Date of Patent: Jul. 24, 2001

(54) HAIR AND SKIN TREATMENT PRODUCT

(76) Inventor: Joseph Lizzi, 84 Patrician Court, Bradford, Ontario (CA), L3Z 1B4

( * ) Notice: Subject to any disclaimer, the term of this patent is extended or adjusted under 35 U.S.C. 154(b) by 0 days.

(21) Appl. No.: 09/351,826

(22) Filed: Jul. 12, 1999

Related U.S. Application Data

(63) Continuation-in-part of application No. 08/965,565, filed on Nov. 6, 1997, now abandoned.

(51) Int. Cl.[7] .................................. A61K 7/06; A61K 7/11
(52) U.S. Cl. ................ 424/70.12; 424/70.1; 424/400; 424/70.11; 424/70.6
(58) Field of Search ........................ 424/400, 401, 424/47, 59, 62, 69, 70.1, 70.2, 70.6, 70.7, 70.9, 70.11, 70.12, 70.121

(56) References Cited

U.S. PATENT DOCUMENTS

| | | | |
|---|---|---|---|
| 4,358,286 | 11/1982 | Grollier et al. | 8/405 |
| 4,401,651 | 8/1983 | Knutson | 424/80 |
| 4,656,029 | 4/1987 | Grollier et al. | 424/47 |
| 4,839,168 | 6/1989 | Abe et al. | 424/74 |
| 4,885,157 | 12/1989 | Fiaschetti | 424/59 |
| 4,927,627 | 5/1990 | Schrader et al. | 424/62 |
| 4,933,177 | 6/1990 | Grollier et al. | 424/74 |
| 4,948,577 | 8/1990 | Hara | 424/59 |
| 5,006,331 | 4/1991 | Gaskin | 424/70 |
| 5,116,607 | 5/1992 | Jones | 424/70 |
| 5,215,760 | 6/1993 | Kavoussi et al. | 424/680 |
| 5,411,741 | 5/1995 | Zaias | 424/450 |
| 5,427,776 | 6/1995 | Isnard | 424/70.1 |
| 5,518,722 | 5/1996 | Szaloki et al. | 424/195.1 |
| 5,804,168 | 9/1998 | Murad | 424/59 |

*Primary Examiner*—Dameron L. Jones
(74) *Attorney, Agent, or Firm*—Ridout & Maybee

(57) ABSTRACT

A hair treating and skin care preparation for use alone or as a component in other preparations, for use in hair dyeing, bleaching, hair conditioning or skin treatments comprises a mixture of hydrogen peroxide, a silicon component selected from the group consisting of silica gel, silicic acid anhydride and mixtures thereof, and a relatively small amount of Aloe vera gel. Prior to use, at least 1.5 g of leaf material from an Aloe vera plant per liter of the hydrogen peroxide, silicon component and aloe vera mixture are placed in the mixture for at least 12 hours in order to dissolve active components from the leaf material and then the undissolved remnants are removed. The preparation can be used for treating skin conditions such as a rash or eczema. A similar preparation can also be combined with water and one or more herbs to provide a health providing remedy that is applied to the skin.

23 Claims, No Drawings

HAIR AND SKIN TREATMENT PRODUCT

The present application is a continuation-in-part of application Ser. No. 08/965,565 which was filed Nov. 6, 1997 now abandoned.

BACKGROUND OF THE INVENTION

This invention relates to compounds and preparations used for the purpose of hair coloring, hair conditioning and skin care, and including preparations for good health and remedies for conditions affecting health.

A variety of products and preparations are already known for both conditioning hair and for coloring the hair of humans. It is also well known to bleach or whiten hair using products such as hydrogen peroxide. Hair conditioners are commonly used to soften hair and to prevent hair from becoming damaged as a result of other types of hair treatments, such as hair shampoos.

Hair coloring solutions and preparations have been used for years both by professionals and by end users at home. However, there are some known problems that exist with existing hair coloring products, including the difficulty that many of these products have in covering grey hair adequately. Another problem is that hair coloring preparations and solutions can dry out fairly quickly, rendering them unsuitable for use. A further difficulty with hair treating products, including hair colorants, bleaches and shampoos, is that they can cause scalp irritation, particularly, if the user has sensitive skin.

U.S. Pat. No. 4,927,627 issued May 22, 1990 to Henkel Kommanditgesellschaft auf Aktien describes emulsion-foam hydrogen peroxide compositions in the form of an oil-in-water emulsion containing oil or fatty components, emulsifiers and hydrogen peroxide and, in addition, a thickening agent. These compositions are said to be particularly suitable as an oxidizing component in processes for the dyeing or lightening of hair resulting in improved depth of color. The oily component is selected from the group consisting of oils, fatty alcohols and mixtures thereof.

U.S. Pat. No. 4,656,029 issued Apr. 7, 1987 to L'Oreal describes a cosmetic composition containing, as an agent protecting against light, pure aloesin or an aloe extract containing at least 40% of aloesin and less than 5% of barbaloin in a cosmetically acceptable medium. This cosmetic composition can be a sunscreen or a cosmetic stabilized against light and can be applied on skin or to hair.

It is believed that the use of aloe extracts is widespread in the cosmetic field. The Aloe genus covers a wide variety of species. Among the components which may appear in aloe extracts are barbaloin, aloe-emodin, aloenin, aloesin and aloesone.

Extracts and gels produced from Aloe vera plants, in particular the Aloe barbadensis Miller plant, are known to have beneficial health effects, including usefulness as antiseptics, analgesics, and as anti-inflammatory agents. It is also believed that the application of Aloe vera gel to the skin can stimulate cell growth. It is recognized that Aloe vera gel has the ability to penetrate deeply into the layers of human skin. In its gel form it is a known remedy for burns and wounds.

It is an object of the present invention to provide a novel hair treating preparation that can be used as a component in hair dyeing and bleaching and for use in hair conditioning and that can be readily produced using known components including hydrogen peroxide and Aloe vera.

It is a further object of the present invention to provide a novel skin care preparation for use in treating skin conditions, such as a rash or eczema, which preparation can be made inexpensively using known, acceptable components including hydrogen peroxide and Aloe vera.

It is another object of the present invention to provide a preparation for use in skin treatment products and to provide additional health benefits using materials and components which are individually known per se including hydrogen peroxide and a small, effective amount of Aloe vera.

Unless indicated otherwise, measurements given herein are in SI units or in Imperial measure.

SUMMARY OF THE INVENTION

Accordingly, the present invention provides a preparation, suitable for treating hair and skin, comprising a mixture of:
 (a) from 1.5 to 12 parts by weight hydrogen peroxide;
 (b) from 88 to 98.5 parts by weight water;
 (c) from 1.5 to 16 parts by weight of a silicon component selected from the group consisting of silica gel, silicic acid anhydride, and mixtures thereof;
 (d) from 0.25 to 6 parts by weight of Aloe vera; and
 (e) an extract of Aloe leaves produced by placing plant leaf components (a) to (d), in a quantity of at least 1.5 g aloe plant leaf per liter of components (a) to (d), for at least about 12 hours and then removing undissolved leaf remnants.

In a preferred embodiment, the preparation has from 1.5 to 100 g aloe plant leaf per liter of components (a) to (d).

In one embodiment, the preparation also contains herbal or plant remedies.

In another embodiment, the preparation contains effective amounts of at least one ingredient selected from the group consisting of soya bean oil, garlic clove, chickweed, ginseng, ginseng extract, horsetail herb, rosemary, burdock root, yellow dock and Ma Haug herb.

In another embodiment, the preparation is a skin care preparation and contains from 1.5 to 9 parts by weight hydrogen peroxide and from 98.5 to 91 parts by weight water.

In a further embodiment, the preparation is a hair care preparation and contains 1.5 to 9 parts by weight hydrogen peroxide and from 98.5 to 91 parts by weight water, especially from 3 to 12 parts by weight of hydrogen peroxide and from 97 to 88 parts by weight water.

In yet another embodiment, the preparation is diluted with water, provided that the resulting ratio of hydrogen peroxide to water is not less than 1.5 to 98.5.

In a further embodiment, the preparation is diluted with water and at least one herbal or plant remedy suitable for hair conditioning is added, provided that the resulting ratio of hydrogen peroxide to water is not less than 1.5 to 98.5.

In yet another embodiment, the preparation is further mixed with a hair care preparation.

In another embodiment, the preparation is further mixed with a skin care preparation.

The present invention also provides a process for making a preparation, suitable for treating hair and skin, comprising the steps of:
 (a) mixing from 1.5 to 12 parts by weight hydrogen peroxide, from 88 to 98.5 parts by weight water, from 1.5 to 16 parts by weight of a silicon component selected from the group consisting of silica gel, silicic acid anhydride, and mixtures thereof, and from 0.25 to 6 parts by weight of Aloe vera;

(b) adding at least 1.5 g of aloe plant leaf material per liter of the mixture from step (a), allowing to steep for at least about 12 hours and then removing undissolved leaf remnants.

In a preferred embodiment, from 1.5 to 100 g aloe plant leaf per liter of the mixture from step (a) is added in step (b).

In one embodiment, the aloe vera in step (a) is in gel form.

In another embodiment, effective amounts of at least one ingredient selected from the group consisting of soya bean oil, garlic clove, chickweed, ginseng, ginseng extract, horsetail herb, rosemary, burdock root, yellow dock and Ma Haug herb are added in step (a) or step (b).

In another embodiment, the hydrogen peroxide and water are added in a ratio of from 1.5 to 9 parts by weight hydrogen peroxide to from 98.5 to 91 parts by weight water.

In a further embodiment, the hydrogen peroxide and water are added in a ratio of from 3 to 12 parts by weight of hydrogen peroxide to from 97 to 88 parts by weight water.

In yet another embodiment, the preparation is diluted with water in a subsequent step, provided that the resulting ratio of hydrogen peroxide to water is not less than 1.5 to 98.5.

In a further embodiment, the preparation is diluted with water and at least one herbal or plant remedy suitable for hair conditioning is added, provided that the resulting ratio of hydrogen peroxide to water is not less than 1.5 to 98.5.

In yet another embodiment, the preparation produced by the process is further mixed with a hair care preparation.

In another embodiment, the preparation produced by the process is further mixed with a skin care preparation.

DETAILED DESCRIPTION OF THE INVENTION

As indicated hereinabove, the preparation of the present invention contains hydrogen peroxide, water, a silicon component and aloe vera. In addition, the preparation contains active components from aloe vera leaf material which has been steeped in a mixture of the other components. The mixture is treated by adding at least 1.5 g of leaf material of an aloe plant per liter of the mixture, and allowing the leaf material to steep for at least about 12 hours in order to dissolve active components from the leaf or leaves. Dissolution of the active components is preferably undertaken at a temperature from about 15° C. to about 30° C., preferably at room temperature, e.g. between about 18° C. to 25° C. Then the undissolved remnants of the leaf material are removed prior to use of the preparation. Removal is preferably by filtration.

In a preferred form, the preparation is made using 20 volume hydrogen peroxide solution (6% hydrogen peroxide), and the resulting preparation is diluted with about an equal volume water. The hydrogen peroxide concentration in the final mixture is equivalent to about 10 volume hydrogen peroxide solution (about 3% hydrogen peroxide).

When the preparation is for use in treating skin conditions, such as a rash or eczema, the hydrogen peroxide solution preferably contains peroxide in an amount of 1.5 to 9 parts by weight and water in an amount of 98.5 to 91 parts by weight. This corresponds to aqueous hydrogen peroxide solutions having strengths ranging between 5 volume and 30 volume. It has been found that at lower concentrations of hydrogen peroxide, bacteria tend to form in the solution after a period of time. For example, using 5 volume hydrogen peroxide, the preparation would need to be used within about 3 weeks of manufacture, in order to avoid bacteria formation. Using 30 volume peroxide, the preparation would last for at least two years without bacteria formation. For this reason, for commercial sale, preparations with 30–40 volume hydrogen peroxide are preferred. They can then be diluted with water prior to use, as long as the dilution does not lower the hydrogen peroxide below the equivalent of 5 volume peroxide in water.

According to still another aspect of the invention, a preparation for use in skin treatment products and other health remedies comprises a mixture of a premixed preparation made according to the above-mentioned invention (including hydrogen peroxide; a component selected from the group consisting of silica gel, silicic acid anhydride, and mixtures thereof; Aloe vera; and the active components from Aloe leaf material), and water in an amount at least equal in volume to the premixed preparation.

A preferred form of this preparation is prepared using the aforementioned premixed preparation and water in a ratio of about 7 liters premixed preparation to 24 liters of water, provided that the hydrogen peroxide concentration does not go below 1.5%, i.e. equivalent to 5 volume hydrogen peroxide solution.

With respect to the strength of the hydrogen peroxide that should be used to make the hair treating preparation of the invention, as indicated, both 20 volume and 30 volume hydrogen peroxide have been tested and have proven to work satisfactorily for hair treatment including hair coloring and hair conditioning but 40 volume and 60 volume hydrogen peroxide, unless substantially diluted with water, are too harsh for most human skin and therefore are not recommended for direct contact with the skin. On the other hand, a hydrogen peroxide solution which is too weak would result in a preparation that would have few, if any, advantages. Accordingly, 2.5 volume hydrogen peroxide is not recommended. Ten volume hydrogen peroxide that has not been diluted further with water or distilled water is the minimum strength that should be used in making a hair treating preparation while 5 volume hydrogen peroxide (that has not been diluted further) is the minimum strength that should be used for a skin care preparation or hair care preparation made in accordance with this invention.

With respect to the minimum or maximum amounts of silica gel or silicic acid anhydride that should be used in the preparation, testing has shown that if the amount of silica gel is reduced to only one half ounce per four cups of 20 volume hydrogen peroxide, the resulting preparation is not as satisfactory as where greater amounts are used (see above examples). Some skin irritation, probably due to the hydrogen peroxide resulted where the silica gel was reduced to this low level. Also, testing has shown that greater amounts of silica gel and Aloe vera gel can be used when hydrogen peroxide having a strength substantially greater than 20 volume hydrogen peroxide is used.

Preferably, the Aloe vera is provided as substantially a pure gel in an amount at least about ¼ fluid ounce per an amount of hydrogen peroxide equivalent to four cups (Imperial measure) of 20 volume hydrogen peroxide.

The Aloe vera components, i.e. the aloe vera and the aloe vera leaves, in the preparations of this invention can be produced from a variety of known aloe species. However, the most common species for the production of Aloe vera gel is Aloe barbadensis or Aloe barbadensis Miller and this is the preferred species for Aloe vera gel used in this invention. The leaves used in producing the preparations described herein came from aloe plants sold under the name Aloe Variegata. However, the leaves from Aloe barbadensis Miller plants can be used in the production of preparations according to this invention. Leaves from other aloe plant species can also be used, if desired.

As indicated hereinbefore, portions of aloe leaves are added to the mixture of the hydrogen peroxide, the silicon component and aloe vera, so that active ingredients from the aloe leaf may be dissolved in the mixture. Whole aloe leaves may be used or portions of aloe leaves. Suitable leaf sizes vary from about 2.5 cm to about 20 cm wide and from about 10 cm to 650 cm long. Preferred weights or sizes of the leaves will depend in part on the desired use of the preparation and can be determined through easy experimentation. At least about 1.5 g of leaf material is added per liter of hydrogen peroxide, silicon component and aloe vera mixture. Preferably from about 1.5 g to 100 g is added.

With respect to the amount of Aloe vera gel that can be used in the preparation, tests have also shown that substantially increased amounts of Aloe vera gel (higher than the amounts indicated in the above examples) resulted in preparations that did not work as well. With increased amounts, the Aloe vera gel does not dissolve properly and the resulting preparation is less creamy. It is therefore recommended that the amount of Aloe vera gel per four cups of 20 volume hydrogen peroxide not exceed about 2½ fluid ounces. Tests have also shown that reducing the amount of Aloe vera gel to substantially less than ¼ fluid ounce per four cups of 20 volume hydrogen peroxide also results in a preparation that is less satisfactory because it can cause some skin irritation in some users. It is recommended that no less than a minimum ⅛ fluid ounce of Aloe vera gel be used for every four cups of 20 volume hydrogen peroxide and preferably one quarter ounce of gel for this amount of hydrogen peroxide.

With respect to the water that is mixed with the hydrogen peroxide in producing preparations according to the invention, either natural water or distilled water can be used. If natural water is used, bottled water is preferred in order to avoid water containing any chlorine or other undesirable additives. Natural water that is "hard" due to its mineral contents should normally be avoided, particularly for use in a hair treatment preparation.

According to a first embodiment of the invention, a preferred hair treating preparation for use as a component in hair dyeing and bleaching and for use in hair conditioning can be produced by mixing thoroughly the following components in a suitable container:

4 cups of 20 volume hydrogen peroxide;

4 cups of distilled water;

1 fluid ounce of silica gel; and

¼ fluid ounce of Aloe vera gel (freshly pressed).

After the above ingredients had been thoroughly mixed, two normal size leaves (about 30 g) of the aforementioned Aloe vera plant (freshly picked) were placed in the mixture in order to dissolve the active components of the leaves into the mixture. The leaves were left in the mixture for about 48 hours or longer. The leaves could have been left for longer, if desired. The undissolved remnants of the leaves were then removed from the mixture by filtration. The preparation is useful as a hair treating preparation.

The aforementioned preparation can be mixed with existing hair coloring products to provide an improved hair coloring preparation that has a substantially longer shelf life and that is better able to cover grey hair, a well known problem with many existing hair coloring preparations. Also, use of the present hair treating preparation with existing hair coloring products has been found to increase the length of time that the hair coloring lasts and to reduce substantially or eliminate the harm that can be caused to a user's hair with existing hair coloring products.

Also, tests conducted with the use of the present hair treating preparation in combination with known hair coloring products have shown that the use of applicant's preparation can increase the speed of the hair coloring process or the bleaching process, if a bleach is being used. Further, a truer colour will result with the use of applicant's preparation without an undesirable mineral oil build-up.

With respect to the improved shelf life of hair coloring compounds or bleaching compounds when combined with the present hair treating preparation, tests have shown that the mixed combination of applicant's preparation and a known hair coloring product or bleach generally lasts and remains usable for at least a 24 hour period. In addition, this mixture remains moist for up to four days and, even after this period of time, simply by adding further hydrogen peroxide to the mixture, the preparation can be restored to a usable state that can still be used for coloring hair or bleaching hair.

The hair treating preparation of the present invention as described above is also very useful either when used alone or in combination with existing known hair conditioners for conditioning hair and making it soft, manageable and easy to comb, even after drying. Use of the present preparation will leave the user's hair shiny, giving it a very attractive appearance.

The above described preparation is also extremely useful as a skin care preparation capable of treating skin conditions such as rashes and eczema. Regular use of the preparation on skin over a period of time can relieve itching and reduce redness. The preparation can help to soften rough, damaged skin. In one test of the preparation, regular use of the preparation over a period of eight days resulted in substantial improvement to a user's hands which were dry and cracked.

Tests have also been conducted on preparations using hydrogen peroxide, silica gel and Aloe vera gel but without the subsequent dissolving of leaves of an aloe plant in the mixture and without the use of any herbs. Such tests have shown that the resulting preparation is not as satisfactory for hair treating or hair conditioning as the preparation made with the use of one or more dissolved leaves from an Aloe vera plant. When the step of dissolving leaves in the mixture is not used, more skin irritation can result from use of the preparation. It appears that the hydrogen peroxide in this preparation (without the active components from the leaves) causes some burning effect that is noticeable by at least some users of the product.

The following examples illustrate the invention without, however, restricting it.

EXAMPLE 1

20 volume hydrogen peroxide 4 cups (32 ounces)

silica gel 2 fluid ounces

Aloe vera gel (freshly pressed) 1 fluid ounce leaves of Aloe vera plant 2 (about 30 g)

The hydrogen peroxide, silica gel and Aloe vera gel were thoroughly mixed in a suitable container, for example, a container approximately 1 liter in size. Then the Aloe vera plant leaves were added to the mixture and left for a period of 24 hours in order to permit the active components in the leaves to be dissolved. Then the undissolved remnants of the leaves were removed by filtration, prior to use of the preparation.

The resulting preparation was tested by mixing with known hair coloring products and found to provide distinct hair coloring advantages as indicated above, including faster and more even hair coloring, without undesirable skin irritation.

The preparation of Example 1 was also tested without the use of any leaves from an Aloe vera plant and, although the resulting preparation was found to be still useful for hair coloring purposes and to have advantages over existing hair coloring components, the preparation did cause some skin irritation in a few cases where the users had sensitive skin.

EXAMPLE 2

20 volume hydrogen peroxide 4 cups silica gel 6 fluid ounces

Aloe vera gel (freshly pressed) ¼ fluid ounce

Aloe vera leaves 2 (about 30 g)

Again, the hydrogen peroxide, silica gel and Aloe vera gel were mixed thoroughly and then the two Aloe vera leaves were placed in the mixture for 24 hours in order to dissolve the active components. The leaf remnants thereafter were removed by filtration. It was found that this preparation was less desirable than the preparation of Example 1 as the silica gel did not dissolve completely and the preparation had a less pleasant feel than that of Example 1. Nevertheless, testing of this preparation indicated that it did have some of the advantages of Example 1 when used in conjunction with hair coloring or hair bleaching products.

EXAMPLE 3

30 volume hydrogen peroxide 4 cups silica gel 3 fluid ounces

Aloe vera gel 1½ fluid ounces

Aloe vera leaves 2 (about 30 g)

As in Example 1, the hydrogen peroxide, silica gel and Aloe vera gel were mixed thoroughly and then the two Aloe vera leaves were placed in the mixture for a 24 hour period in order to dissolve the active components in the Aloe vera leaves. The remnants of the leaves were then removed by filtration, prior to use of the preparation with hair coloring and hair bleaching preparations.

Testing of this preparation found it to be excellent for both hair coloring and hair bleaching and also very useful as a hair conditioner. The preparation was found to have the same advantages for hair coloring and hair bleaching as the first described preparation set out above and Example 1.

EXAMPLE 4

30 volume hydrogen peroxide 4 cups silica gel 2 fluid ounces

Aloe vera gel 1 fluid ounce

Aloe vera leaves 2 (about 30 g)

The same procedure was followed as stated above for Example 3, the two leaves being allowed to dissolve in the mixture for a period of 24 hours. However, in this case, the resulting preparation, when tested, was found to be less desirable as a hair treatment preparation as it resulted in some skin irritation. This was felt to be due to the relatively high strength of the hydrogen peroxide combined with the relatively low amounts of silica gel and Aloe vera gel.

EXAMPLE 5

Preparation of Example 1 7 fluid ounces water 24 fluid ounces soya bean oil 50 ml garlic clove (pressed) 5 ml In this example, a premix in the form of a preparation made according to Example 1 as set out above was provided. This premix was combined with the other 3 ingredients listed above in a suitable container and mixed thoroughly. The resulting preparation is a good preparation for skin care and, in particular, for treating skin conditions such as infected skin, rashes and pimples.

In the above example and in the examples described hereinafter, known herbal and plant remedies can be employed in combination with a preparation made according to the invention. It is known to use these herbal and plant remedies with warm water in order to provide benefits to the skin or other health benefits. For example, with reference to chickweed used in Example 6 below, it is known to use this plant material in warm water to heal wounds, relieve pain and treat skin rashes and conditions. However, this known plant remedy suffers from the disadvantage that it loses its beneficial effects as the water cools off. By using the known herb or plant in combination with a preparation according to the present invention, this problem can be avoided. The preparation can be applied without the need to warm it beforehand and without the need to use a warm wet cloth (as has been often done in the past with such herbal and plant remedies).

EXAMPLE 6

Premixed preparation of Example 1 7 fluid ounces water 24 fluid ounces chickweed 5 ml These ingredients were mixed thoroughly in a suitable container. The resulting preparation is useful in healing wounds, in relieving joint pain, and in the treatment of skin rashes or eczema and can be used without the need for warming the preparation first.

EXAMPLE 7

Premixed preparation of Example 1 7 fluid ounces water 24 fluid ounces rosemary 5 ml The above listed ingredients were mixed thoroughly. The resulting preparation can be used as a final rinse after hairwashing or other hair treatment in order to treat or prevent dandruff. This preparation is usually used in a warm condition for the comfort of the user.

EXAMPLE 8

Premixed preparation of Example 1 7 fluid ounces water 24 fluid ounces ginseng extractum 10 ml Panax (trade mark) ginseng extractum was used in this reparation. Again, the above listed ingredients were mixed thoroughly to produce a preparation for application to the skin. The resulting preparation, when applied in effective amounts to the skin, is suitable as a stimulant and can help improve the user's immune system by being absorbed into the skin.

EXAMPLE 9

Premix preparation of Example 1 7 fluid ounces water 24 fluid ounces horsetail herb 5 ml Again, the above listed ingredients were mixed thoroughly in a suitable container. The resulting skin care preparation is useful for helping to stop minor bleeding and as an anti-inflammatory tissue healer. The same preparation can also be used to treat acne conditions and eczema.

EXAMPLE 10

Premixed preparation of Example 1 7 fluid ounces
water 24 fluid ounces
burdock root 5 ml The above listed ingredients were thoroughly mixed. The resulting preparation is useful as a skin cleanser and to heal skin blemishes.

EXAMPLE 11

Premixed preparation of Example 1 7 fluid ounces
water 24 fluid ounces
Ma Haug herb 5 ml The above listed ingredients were mixed thoroughly in a suitable 1 liter container. The resulting preparation, when applied to a person's skin, is absorbed into the skin and acts as a tonic, increasing the user's energy levels.

EXAMPLE 12

Premixed preparation of Example 1 7 fluid ounces
water 24 fluid ounces
yellow dock 5 ml The above listed ingredients were mixed thoroughly. The resulting preparation is a useful skin preparation that can be used to treat skin conditions such as minor skin eruptions and boils.

EXAMPLE 13

Premixed preparation of Example 1 7 ounces
water 24 ounces
soya bean oil 50 ml
garlic clove 5 ml
chickweed 5 ml
ginseng (Panax ginseng extractum) 5 ml
horsetail 5 ml All of the above listed ingredients were mixed thoroughly in a suitable mixing container. The resulting preparation has beneficial health effects when applied in effective amounts to the skin in affected areas. In particular, the preparation is useful for treating sprains and the pain caused thereby and for the treatment of other types of localized pain. One major advantage of this preparation is that it can be applied directly and externally to the skin area and it avoids the need to take any of the herbal remedies internally by means of a tea or otherwise. Also, when the herbs are mixed with the basic mixture of the invention, the effective shelf life of the preparation is quite long. In fact, tests have shown that the shelf life for such preparations in a sealed container is at least 4 months.

EXAMPLE 14

Four formulations (identified hereinafter as A, B, C and D) were prepared to yield hydrogen peroxide concentrations of 3%, 6%, 9% and 12% hydrogen peroxide in water solution, i.e. percentages exclusive of the presence of the other ingredients. The formulations were:

A)
8.3 parts 35% hydrogen peroxide solution
88.0 parts distilled water
3.0 parts silica gel
0.7 parts aloe vera gel
2 leaves (about 30 g) of aloe vera per liter of the formulation B)
15.6 parts 35% hydrogen peroxide solution
75.5 parts distilled water
5.9 part silica gel
3.3 parts aloe vera gel
2 leaves (about 30 g) of aloe vera per liter of the formulation C)
22.2 parts 35% hydrogen peroxide solution
64.4 parts distilled water
9.0 part silica gel
4.4 parts aloe vera gel
2 leaves (about 30 g) of aloe vera per liter of the formulation D)
28.2 parts 35% hydrogen peroxide solution
54.1 parts distilled water
11.8 part silica gel
5.9 parts aloe vera gel
2 leaves (about 30 g) of aloe vera per liter of the formulation The peroxide solution, water, silica gel and aloe vera gel were mixed together first and then the aloe vera leaves were placed in the mixture and allowed to remain for about 48 hours at room temperature (about 21° C.). Subsequently, remains of the aloe leaves were removed by filtering.

Although the preparations according to the invention may be made using silica gel, silicic acid anhydride may be used instead in the making of these preparations and also various mixtures of silica gel and silicic acid anhydride. One particularly suitable silica gel product is that sold by Naka Sales Limited of Toronto, Ontario, bearing number 52144-03R. This particular product is manufactured in Germany and includes silicic acid anhydride in the mixture.

It will be readily apparent to those skilled in the present art that various modifications and changes can be made to the described hair treating and skin care preparations without departing from the spirit and scope of this invention.

Accordingly, all such modifications and changes as fall within the scope of the appended claims are intended to be part of this invention.

What is claimed is:

1. A preparation for treating hair and skin, comprising a mixture of:
   (a) from 1.5 to 12 parts by weight hydrogen peroxide;
   (b) from 88 to 98.5 parts by weight water;
   (c) from 1.5 to 16 parts by weight of a silicon component selected from the group consisting of silica gel, silicic acid anhydride, and mixtures thereof;
   (d) from 0.25 to 6 parts by weight of Aloe vera; and
   (e) an extract of Aloe leaves produced by placing aloe plant leaf in components (a) to (d) in a quantity of at least 1.5 g aloe plant leaf per liter of components (a) to (d), for at least about 12 hours and then removing undissolved leaf remnants.

2. A hair treating preparation according to claim 1 wherein hydrogen peroxide is present in an amount of from 3 to 12 parts by weight and water is present in an amount of from 97 to 88 parts by weight.

3. A hair treating preparation according to claim 2 wherein the active components of Aloe leaves have been dissolved in the mixture by placing at least one leaf in the mixture for at least 24 hours.

4. A hair treating preparation according to claim 2 wherein said Aloe vera is in gel form.

5. A hair treating preparation according to claim 2, for treating dandruff, which additionally contains an effective amount of rosemary.

6. A preparation according to claim 1 which is diluted with an additional amount of water, wherein the resulting ratio of hydrogen peroxide to water is not less than 1.5 to 98.5.

7. A skin care preparation according to claim 1 wherein hydrogen peroxide is present in an amount of from 3 to 12 parts by weight and water is present in an amount of from 97 to 88 parts by weight.

8. A skin care preparation according to claim 7 wherein said Aloe vera is in gel form.

9. A skin care preparation according to claim 7 for treating skin conditions, which additionally contains an effective amount of a least one ingredient selected from the group consisting of soya bean oil, garlic clove, chickweed, ginseng, ginseng extract, rosemary, horsetail herb, burdock root, yellow dock and Ma Haug herb.

10. A skin care preparation according to claim 7 wherein said at least one leaf is from an Aloe barbadensis Miller plant.

11. A preparation according to claim 1 wherein the aloe plant leaf is added in an amount of from 1.5 to 100 g per liter of components (a) to (d).

12. A skin treatment preparation said preparation comprising a mixture of:
   (a) a premixed preparation prepared in accordance with claim 7; and
   (b) additional water in an amount wherein the resulting ratio of hydrogen peroxide to water is not less than 1.5 to 98.5.

13. A skin care preparation according to claim 9 which contains an effective amount of soya bean oil and garlic clove.

14. A skin care preparation according to claim 9 which contains an effective amount of the herb chickweed.

15. A skin care preparation according to claim 9 which contains an effective amount of the herb rosemary.

16. A skin care preparation according to claim 9, for use as a stimulant, which contains an effective amount of an ingredient selected from the group consisting of ginseng and ginseng extract and mixtures thereof.

17. A skin care preparation according to claim 9 which contains an effective amount of burdock root.

18. A skin care preparation according to claim 9, for use in improving energy levels in humans, which contains an effective amount of the herb ma haug.

19. A skin care preparation according to claim 9, for use in treating skin eruptions and boils, which contains an effective amount of yellow dock.

20. A skin care preparation according to claim 9, for use as an anti-inflammatory, which contains an effective amount of the herb horsetail.

21. A skin care preparation according to claim 9, for use in relieving pain, which contains a mixture of garlic clove, chickweed, ginseng, horsetail, and soya bean oil.

22. A process for preparing a preparation, for treating hair and skin, comprising the steps of:
   A) mixing a combination of:
      (a) from 1.5 to 12 parts by weight hydrogen peroxide;
      (b) from 88 to 98.5 parts by weight water;
      (c) from 1.5 to 16 parts by weight of a silicon component selected from the group consisting of silica gel, silicic acid anhydride, and mixtures thereof;
      (d) from 0.25 to 6 parts by weight of Aloe vera;
   B) subsequently steeping at least 1.5 g aloe leaf per liter of the combination for at least 12 hours; and
   C) after step B) removing undissolved leaf remnants.

23. A process according to claim 22 wherein the amount of aloe leaf added in step (B) is from 1.5 to 100 g per liter of the combination.

* * * * *